United States Patent
Furuta et al.

(10) Patent No.: US 9,302,964 B2
(45) Date of Patent: Apr. 5, 2016

(54) METHOD FOR PURIFYING TETRAFLUOROPROPENE

(71) Applicant: ASAHI GLASS COMPANY, LIMITED, Tokyo (JP)

(72) Inventors: Shoji Furuta, Tokyo (JP); Tetsuo Otsuka, Tokyo (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

(21) Appl. No.: 14/749,877

(22) Filed: Jun. 25, 2015

(65) Prior Publication Data

US 2015/0291490 A1 Oct. 15, 2015

Related U.S. Application Data

(63) Continuation of application No. PCT/JP2013/081448, filed on Nov. 21, 2013.

(30) Foreign Application Priority Data

Dec. 27, 2012 (JP) ................................ 2012-285248

(51) Int. Cl.
C07C 17/386 (2006.01)
C07C 17/18 (2006.01)
C07C 17/395 (2006.01)

(52) U.S. Cl.
CPC ............... *C07C 17/386* (2013.01); *C07C 17/18* (2013.01); *C07C 17/395* (2013.01)

(58) Field of Classification Search
CPC ............................. C07C 17/38; C07C 17/395

USPC .......................................... 570/175, 177, 178
See application file for complete search history.

(56) References Cited

U.S. PATENT DOCUMENTS

| | | | |
|---|---|---|---|
| 2,931,840 A | 4/1960 | Marquis | |
| 9,023,233 B2 | 5/2015 | Furuta et al. | |
| 2005/0233923 A1 | 10/2005 | Singh et al. | |
| 2007/0100175 A1 | 5/2007 | Miller et al. | |
| 2011/0270001 A1 | 11/2011 | Ishihara et al. | |
| 2012/0151959 A1 | 6/2012 | Rached | |
| 2013/0105296 A1 | 5/2013 | Chaki et al. | |
| 2015/0005537 A1 | 1/2015 | Furuta et al. | |
| 2015/0005538 A1 | 1/2015 | Furuta et al. | |

FOREIGN PATENT DOCUMENTS

| | | |
|---|---|---|
| JP | 2008-506793 | 3/2008 |
| JP | 2009-513719 | 4/2009 |
| JP | 2010-202640 | 9/2010 |
| WO | WO 2011/030026 | 3/2011 |
| WO | WO 2012/011609 | 1/2012 |
| WO | WO 2012/0105700 | 8/2012 |

OTHER PUBLICATIONS

International Search Report issued Feb. 18, 2014 in PCT/JP2013/081448 filed Nov. 21, 2013.

*Primary Examiner* — Elvis O Price
(74) *Attorney, Agent, or Firm* — Oblon, McClelland, Maier & Neustadt, L.L.P.

(57) ABSTRACT

To provide a method for efficiently separating 2,3,3,3-tetrafluoropropene (HFO-1234yf) and chloromethane (R40) from a composition containing HFO-1234yf and R40. A method for separating HFO-1234yf containing substantially no R40, which comprises bringing an azeotropic composition or azeotrope-like composition of H FO-1234yf and R40 into contact with a specific extraction solvent.

5 Claims, 1 Drawing Sheet

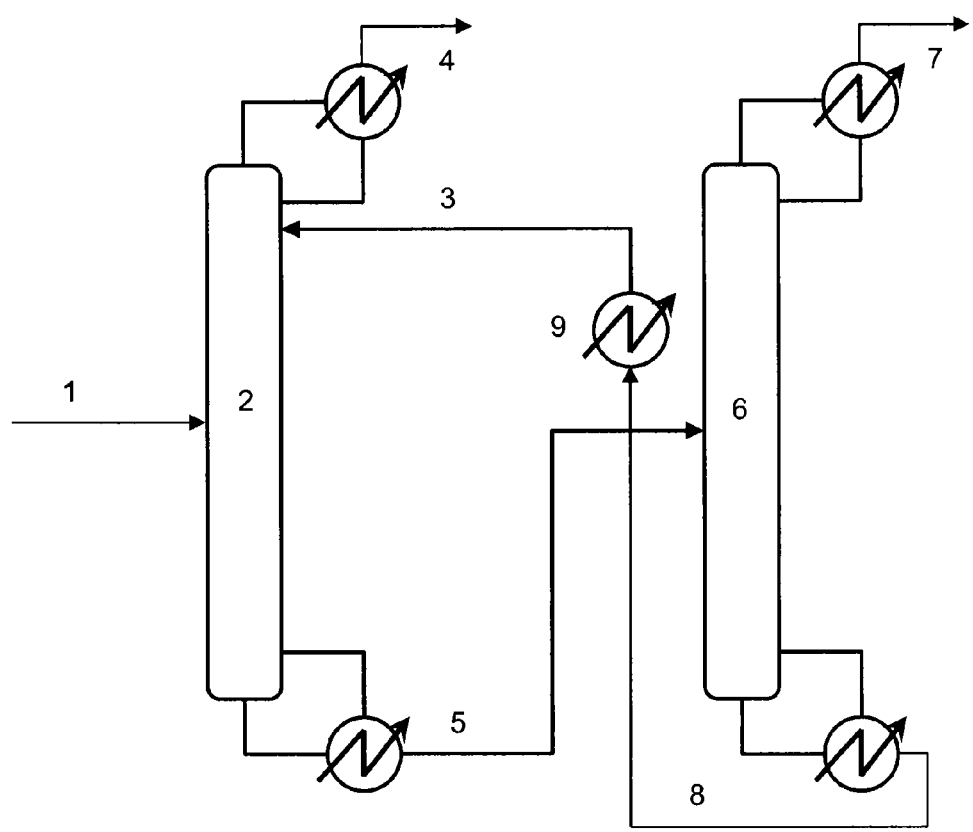

METHOD FOR PURIFYING TETRAFLUOROPROPENE

CROSS-REFERENCE TO RELATED APPLICATIONS

This application is a Continuation of PCT/JP2013/081448 filed on Nov. 21, 2013. This application is based upon and claims the benefit of priority to Japanese Application No. 2012-285248 filed on Dec. 27, 2012, the entire contents of which are incorporated herein by reference.

BACKGROUND OF THE INVENTION

TECHNICAL FIELD

The present invention relates to a method to obtain 2,3,3,3-tetrafluoropropene (hereinafter sometimes referred to as "HFO-1234yf") or chloromethane (hereinafter sometimes referred to as "R40") from a composition containing 2,3,3,3-tetrafluoropropene and chloromethane.

BACKGROUND ART 2,3,3,3-tetrafluoropropene has attracted attention as a new refrigerant to be substituted for 1,1,1,2-tetrafluoroethane (HFC-134a) which is a greenhouse gas.

Here, in this specification, with respect to a halogenated hydrocarbon, in brackets after its chemical name, an abbreviated name of the compound is indicated, and as the case requires, instead of the chemical name, its abbreviated name is used.

Further, a method for producing HFO-1234yf by one reaction involving thermal decomposition, from a raw material containing a chlorofluorocarbon, has been proposed.

As such a method, for example, Patent Document 1 proposes a method to obtain HFO-1234yf by heating and decomposing a mixture of chloromethane (R40) and chlorodifluoromethane (R22) and/or tetrafluoroethylene (TFE) to a temperature of from 700 to 950° C. in a reactor by means of a conventional heating means such as an electric heater (Patent Document 1).

Here, in a case where HFO-1234yf is to be produced by the above method, the obtainable reaction mixture contains, in addition to the desired substance HFO-1234yf, unreacted raw materials such as R40. From an industrial viewpoint, in addition to purifying the reaction mixture to obtain HFO-1234yf as a product, recycle of R40 for the reaction by purification from the reaction mixture has also been desired.

PRIOR ART DOCUMENT

Patent Document

Patent Document 1: U.S. Pat. No. 2,931,840

DISCLOSURE OF INVENTION

Technical Problem

The boiling points of HFO-1234yf and R40 are respectively −29° C. and −24° C. (under atmospheric pressure) and close to each other and thus separation of them by distillation is difficult.

In the method disclosed in the above background art, as a method for producing HFO-1234yf, the raw material R40 is included, and thus a method to efficiently obtain HFO-1234yf or R40 from a composition containing HFO-1234yf and R40 has been desired.

The present inventors have found that when HFO-1234yf and R40 are to be separated from a composition containing them, an azeotropic composition or azeotrope-like composition forms, and they cannot readily be separated.

To separate a composition which is difficult to separate by conventional distillation, a separation method characterized by bringing the composition into contact with a compound having compatibility with a certain substance in the composition, for example, extractive distillation or absorption, has been known.

When such separation by extractive distillation or absorption is applied to a composition containing HFO-1234yf and R40, it is necessary to use a compound having a high relative volatility of HFO-1234yf based on R40. However, it is difficult to predict the relative volatility of HFO-1234yf based on R40 with respect to a certain compound, or to predict the relative volatility of R40 based on HFO-1234yf with respect to a certain substance. Thus, in the method of separating, for example, HFO-1234yf from R40, by extractive distillation, absorption or the like, it is not possible to predict which substance should be used.

Under these circumstances, it is an object of the present invention to provide a method for efficiently separating HFO-1234yf or R40 from a composition containing HFO-1234yf and R40.

Solution to Problem

The present inventors have found it possible to separate HFO-1234yf and R40 from an azeotropic composition or azeotrope-like composition of them and further found a solvent to efficiently separate them, and accomplished the present invention.

That is, the present inventors have conducted extensive studies on various substances and as a result, found that the relative volatility of HFO-1234yf based on R40 changes by bringing the azeotropic composition or azeotrope-like composition into contact with a specific compound, and accomplished the present invention.

That is, the present invention provides the following.

1. A method for producing 2,3,3,3-tetrafluoropropene, which comprises binging an azeotropic composition or azeotrope-like composition of 2,3,3,3-tetrafluoropropene and chloromethane into contact with an extraction solvent to obtain 2,3,3,3-tetrafluoropropene containing substantially no chloromethane.

2. The method according to the above 1, wherein as the extraction solvent, at least one compound selected from the group consisting of a hydrocarbon, a chlorinated hydrocarbon, an alcohol, an ether, a nitrile, a ketone, a carbonate, an amine, an ester and a sulfoxide, which contains no fluorine atom, a fluorinated compound having a fluorination degree of less than 0.8 and having a polar group or a fluorinated compound having a fluorination degree of less than 0.9 and having no polar group, is used.

3. The method according to the above 2, wherein the hydrocarbon is pentane, hexane, heptane, octane, nonane, decane, undecane or dodecane, the chlorinated hydrocarbon is dichloromethane, trichloromethane, perchloromethane, 1,2-dichloropropane or perchloroethylene, the alcohol is methanol, ethanol, propanol, butanol or pentanol, the ether is 1,3-dioxolane or tetrahydrofuran, the nitrile is acetonitrile, the ketone is acetone, methyl ethyl ketone, diethyl ketone or methyl isobutyl ketone, the carbonate is dimethyl carbonate, the amine is dimethylformamide, dimethylacetamide, N-methylpyrrolidone or N-formylmorpholine, the ester is γ-butyrolactone, and the sulfoxide is dimethyl sulfoxide.

4. A method for producing chloromethane containing substantially no 2,3,3,3-tetrafluoropropene from an azeotropic composition or azeotrope-like composition of 2,3,3,3-tetrafluoropropene and chloromethane, which comprises bring the composition into contact with an extraction solvent.

5. The method according to the above 4, wherein as the extraction solvent, a fluorinated compound having a fluorination degree of at least 0.8 and having a polar group or a fluorinated compound having a fluorination degree of at least 0.9 and having no polar group, is used.

Advantageous Effects of Invention

According to the present invention, a method for efficiently separating 2,3,3,3-tetrafluoropropene (HFO-1234yf) and chloromethane (R40) from a composition containing HFO-1234yf and R40.

BRIEF DESCRIPTION OF DRAWING

FIG. 1 is a view schematically illustrating a method for efficiently separating 2,3,3,3-tetrafluoropropene (HFO-1234yf) and chloromethane (R40) from a composition containing HFO-1234yf and R40.

DESCRIPTION OF EMBODIMENTS

Azeotropic Composition

An azeotropic composition comprising HFO-1234yf and R40 of the present invention is a composition wherein the content ratio of HFO-1234yf is 63 mol %, and the content ratio of R40 is 37 mol %, and has a boiling point of 41.3° C. under a pressure of $1.011 \times 10^6$ Pa. The azeotropic composition undergoes no change in its composition when repeatedly subjected to distillation and condensation and thus has such a merit that when it is used in an application to a refrigerant or the like, an extremely stable performance is obtainable. Further, the azeotropic composition has a relative volatility of 1.00 as represented by the following formula.
(Formula to Obtain Relative Volatility)

Relative volatility=(mol % of HFO-1234yf in gas phase/mol % of R40 in gas phase)/(mol % of HFO-1234yf in liquid phase/mol % of R40 in liquid phase)

[Azeotrope-Like Composition]

The azeotrope-like composition comprising HFO-1234yf and R40 of the present invention is a composition wherein the content ratio of HFO-1234yf is from 58 to 78 mol %, and the content ratio of R40 is from 22 to 42 mol %. It undergoes little change in its composition when repeatedly subjected to distillation and condensation. Here, in this specification, an azeotrope-like composition is a composition wherein the relative volatility obtained by the above formula is within a range of 1.00±0.20. Further, the azeotrope-like composition comprising HFO-1234yf and R40 of the present invention has a boiling point of from 41 to 42° C. under a pressure of $1.011 \times 10^6$ Pa.

The azeotrope-like composition of the present invention can be handled substantially in the same manner as the above-described azeotropic composition of the present invention and has such a merit that when it is used in an application to a refrigerant or the like, a stable performance equal to the azeotropic composition is obtainable. Further, in the following description, the azeotrope-like composition will be described as including the azeotropic composition.

In this specification, the term "extractive distillation" is used in a sense used in the technical field of the present invention particularly in the chemical engineering field, and is one type of distillation separation method to be used to separate an azeotropic composition or a liquid composition which is difficult to separate by distillation separation since the boiling points are close to each other.

In the extractive distillation, by adding a third component to a composition mainly comprising two components, the relative volatility of the original composition mainly comprising two components is changed so as to ease the distillation separation. The third component here is called an extraction solvent in this specification.

The extraction solvent is a compound which may be used for extractive distillation and may be one which is not liquid at room temperature, but is present as a liquid when the extractive distillation is carried out. By adding this extraction solvent to an azeotropic composition or a liquid composition which is difficult to separate by distillation separation since the boiling points are close to each other, it is possible to separate either one of the two components, which is not absorbed in the extraction solvent, that is, either component to be separated. Further, the azeotropic composition may contain a small amount of other components.

The present invention provides a method for separating HFO-1234yf containing substantially no R40 from a composition containing HFO-1234yf and R40, which comprises bringing the composition into contact with an extraction solvent.

The present invention further provides a method for separating R40 containing substantially no HFO-1234yf from a composition containing HFO-1234yf and R40, which comprises bring the composition into contact with an extraction solvent.

It is difficult to separate HFO-1234yf and R40 from a composition containing them by distillation since their boiling points are close to each other. In a case where separation by extractive distillation is applied to a composition containing HFO-1234yf and R40, to separate HFO-1234yf for example, it is necessary to use a solvent with a high relative volatility of HFO-1234yf based on R40.

Thus, the present inventors have conductive studies and as a result, found that HFO-1234yf containing substantially no R40 can be separated from a composition containing HFO-1234yf and R40 by using a specific extraction solvent.

Further, they have hound that R40 containing substantially no HFO-1234yf can be separated from a composition containing HFO-1234yf and R40 by using a specific extraction solvent.

The present inventors have conducted studies on effects by the respective compounds in a method for separating HFO-1234yf by extractive distillation from a composition containing HFO-1234yf and R40. As a result, they have obtained results as mentioned hereinafter with respect to the above-described relative volatility.

Heretofore, it has been known that the gas-liquid equilibrium of two components changes in some cases by the presence of a specific compound. In a case where such a compound affects the gas-liquid equilibrium, the relative volatility obtained by the above formula changes.

A compound which may change the relative volatility is called an extraction solvent in this specification.

The relative volatility in a state where no extraction solvent is added (two-components) and the relative volatility when an extraction solvent is added, are compared. It is understood that if the value obtainable by the above formula is increased, such an extraction solvent is an extraction solvent which absorbs R40. By using such an extraction solvent, it is possible to separate 1234yf from a composition containing HFO-1234yf and R40 by extractive distillation.

Whereas, when the value obtainable by the above formula is decreased, such an extraction solvent is considered to be an extraction solvent which absorbs HFO-1234yf. By using such an extraction solvent, it is possible to separate R40 from a composition containing HFO-1234yf and R40 by extractive distillation.

In this specification, an extraction solvent means a solvent which is liquid at room temperature under normal pressure, however, a solvent which is present as a liquid under reaction conditions in a distillation tower for example, is regarded as the extraction solvent of the present invention.

<Separation of HFO-1234yf>

The extraction solvent in the present invention may be at least one compound selected from the group consisting of a hydrocarbon, a chlorinated hydrocarbon, an alcohol, an ether, a nitrile, a ketone, a carbonate, an amine, an ester and a sulfoxide, which contains no fluorine atom.

The hydrocarbon is a compound having only carbon atoms and hydrogen atoms in its molecule. The hydrocarbon is preferably pentane, hexane, heptane, octane, nonane, decane, undecane or dodecane. It is particularly preferably pentane, hexane, heptane, octane, nonane or decane.

The chlorinated hydrocarbon is a hydrocarbon compound having chlorine atoms in its molecule. The chlorinated hydrocarbon is preferably a $C_{1-5}$ chlorinated hydrocarbon, particularly preferably dichloromethane, trichloromethane, perchloromethane, 1,2-dichloropropane or perchloroethylene.

The alcohol is a compound having a hydrogen atom in a hydrocarbon substituted by a hydroxy group. The alcohol is preferably a compound having a hydrogen atom in a $C_{1-8}$ hydrocarbon substituted by a hydroxy group, more preferably methanol, ethanol, propanol, butanol or pentanol. It is particularly preferably methanol, ethanol or butanol.

The ether may be a linear ether having two hydrocarbon groups bonded to an oxygen atom or a cyclic ether having an oxygen atom as an atom constituting a ring. The ether is preferably a $C_{3-5}$ ether, preferably 1,3-dioxolane or tetrahydrofuran.

The nitrile is specifically preferably acetonitrile.

The ketone is specifically preferably dimethyl ketone (acetone) methyl ethyl ketone, diethyl ketone or methyl isobutyl ketone. It is particularly preferably dimethyl ketone or methyl ethyl ketone.

The carbonate is preferably a $C_{3-5}$ aliphatic carbonate, specifically preferably dimethyl carbonate.

The amine is specifically preferably dimethylformamide, dimethylacetamide, N-methylpyrrolidone or N-formylmorpholine.

The ester may be a linear or a cyclic ester. It is preferably a $C_{3-5}$ linear or cyclic ester, specifically preferably γ-butyrolactone.

The sulfoxide is specifically preferably dimethylsulfoxide.

The extraction solvent in the present invention may be a cyclohexane. The cyclohexane is specifically preferably decamethylcyclopentasiloxane.

Further, the extraction solvent in the present invention is preferably a fluorinated compound having a fluorination degree of less than 0.8 and having a polar group. Particularly, the fluorination degree is preferably at most 0.75.

The "fluorination degree" in the present invention is a value calculated in accordance with the following formula.

Fluorination degree=number of fluorine atoms bonded to carbon atoms/(the number of hydrogen atoms bonded to carbon atoms+the number of fluorine atoms bonded to carbon atoms)

In the present invention, the fluorinated compound having a polar group is a compound having a polar group which is an atomic group having polarity, regardless of the presence of fluorine in its molecule, and is a compound having polarity due to the presence of the atomic group in the organic compound. The polar group is specifically preferably an ether group, an ester group, an amide group or a hydroxy group.

As the compound having a polar group, the compound having an ether group is preferably a $C_{3-8}$ compound, the compound having an ester group is preferably a $C_{3-5}$ compound, the compound having an amide group is preferably a $C_{3-5}$ compound, and the compound having a hydroxy group is preferably a $C_{1-8}$ compound.

The above compound in the present invention is specifically preferably $CF_3CH_2OCF_2CF_2H$ (manufactured by Asahi Glass Company, Limited, tradename: AE3000), tetrafluoropropanol (manufactured by Asahi Glass Company, Limited), $CF_3CF_2CF_2CF_2OCF_3$ (manufactured by Sumitomo 3M Limited, tradename: Novec7100) or $CF_3CF_2CF_2CF_2OCH_2CH_3$ (manufactured by Sumitomo 3M Limited, tradename: Novec7200).

Further, the extraction solvent in the present invention is preferably a fluorinated compound having a fluorination degree of less than 0.9 and having no polar group. Particularly, the fluorination degree is preferably at most 0.85.

The above compound in the present invention is specifically preferably $CClF_2CF_2CHClF$ (manufactured by Asahi Glass Company, Limited, tradename; AK225cb), $CF_3CF_2CF_2CF_2CF_2CF_2CH_2CH_3$ (manufactured by Asahi Glass Company, Limited, tradename: AC6000) or $CF_3CF_2CHFCHFCF_3$ (manufactured by Du Pont, tradename: HFC4310).

<Separation of R40>

Further, according to studies by the present inventors, it was found that chloromethane containing substantially no 2,3,3,3-tetrafluoropropene can be separated from a composition containing 2,3,3,3-tetrafluoropropene and chloromethane by using a specific extraction solvent.

The extraction solvent in the present invention is preferably a fluorinated compound having a fluorination degree of at least 0.8 and having a polar group.

The above compound in the present invention is specifically preferably $CF_3CF_2CF(CH_3)OCF(CF_3)_2$ (manufactured by Sumitomo 3M Limited, tradename: Novec7300), a compound represented by the formula (1) (manufactured by Sumitomo 3M Limited, tradename: FC-77), a compound represented by the formula (2) (manufactured by Solvay S.A., tradename: SV-55) or a compound represented by the formula (3) (manufactured by Solvay S.A., tradename: HT-110).

Formula (1)

$$F_2C\underset{F_2C-CF_2}{\overset{O}{\underset{|}{\bigcirc}}}CF-CF_2-CF_2-CF_2-CF_3$$

Formula (2)

$$F_3C-O-\left[\underset{CF_3}{\overset{F_2}{C}}-\overset{F}{\underset{}{C}}-O\right]_m-\left[\overset{}{\underset{F_2}{C}}-O\right]_n-CF_3$$

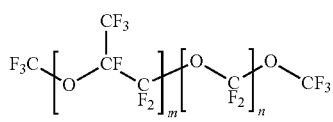

Formula (3)

Further, the extraction solvent in the present invention is preferably a compound having a fluorination degree of at least 0.9 and having no polar group.

The above compound in the present invention is specifically preferably $CF_3CF_2CF_2CF_2CF_2CF_2H$ (manufactured by Asahi Glass Company, Limited, tradename: AC2000) or $CF_3CF_2CF_2CF_2CF_2CF_3$ (manufactured by Sumitomo 3M Limited, tradename: PF-5060).

EXAMPLES

Now, the present invention will be described in further detail with reference to Examples. However, it should be understood that the present invention is by no means restricted thereto.

Example in which Compound Having No Fluorine Atom is Used

Ex. 1

A composition obtained by mixing 176 g of HFO-1234yf, 26 g of R40 and 99 g of methanol was put in a 500 mL autoclave equipped with a pressure meter and gradually heated by an external heater so that the pressure would be $1.011 \times 10^6$ Pa. The composition was adjusted so that the ratio by mol % would be solvent: HFO-1234yf:R40=60:30:10. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the following formula to obtain a relative volatility.

Relative volatility=(mol % of HFO-1234yf in gas phase/mol % of R40 in gas phase)/(mol % of HFO-1234yf in liquid phase/mol % of R40 in liquid phase)

Ex. 2 to 15

In the same manner as in Ex. 1 except that the solvent was changed to a solvent as identified in Table 1, a sample was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility.

TABLE 1

| | Solvent used | Solvent charged amount [g] | HFO-1234yf charged amount [g] | R40 charged amount [g] |
|---|---|---|---|---|
| Ex. 1 | Methanol | 99 | 176 | 26 |
| Ex. 2 | Cyclohexane | 97 | 66 | 10 |
| Ex. 3 | Decane | 91 | 37 | 5 |

TABLE 1-continued

| | Solvent used | Solvent charged amount [g] | HFO-1234yf charged amount [g] | R40 charged amount [g] |
|---|---|---|---|---|
| Ex. 4 | Acetone | 99 | 97 | 14 |
| Ex. 5 | Ethanol | 99 | 122 | 18 |
| Ex. 6 | Hexane | 82 | 54 | 8 |
| Ex. 7 | Dimethylformamide | 119 | 93 | 14 |
| Ex. 8 | Dichloromethane | 166 | 111 | 16 |
| Ex. 9 | Perchloroethylene | 203 | 70 | 10 |
| Ex. 10 | Dichloropropane | 145 | 73 | 11 |
| Ex. 11 | Toluene | 112 | 69 | 10 |
| Ex. 12 | Dimethylacetamide (DMAc) | 118 | 77 | 11 |
| Ex. 13 | Dimethylsulfoxide (DMSO) | 138 | 100 | 15 |
| Ex. 14 | γ-butyrolactone | 141 | 94 | 14 |
| Ex. 15 | N-methylpyrrolidone (NMP) | 129 | 74 | 11 |
| Ex. 16 | Nil | 0 | 186 | 28 |

The results are shown in Table 2. The relative volatility when a non-fluorinated solvent was used was higher than the relative volatility of 0.904 when no solvent was used. This is considered to result from a change in the gas-liquid equilibrium between HFO-1234yf and R40 due to the presence of the non-fluorinated solvent, thus leading to an increase in HFO-1234yf in the gas phase.

TABLE 2

| | Solvent used | Relative volatility |
|---|---|---|
| Ex. 1 | Methanol | 1.201 |
| Ex. 2 | Cyclohexane | 1.347 |
| Ex. 3 | Decane | 1.424 |
| Ex. 4 | Acetone | 1.789 |
| Ex. 5 | Ethanol | 1.911 |
| Ex. 6 | Hexane | 2.036 |
| Ex. 7 | DMF | 2.285 |
| Ex. 8 | Dichloromethane | 2.504 |
| Ex. 9 | Perchloroethylene | 2.544 |
| Ex. 10 | Dichloropropane | 2.674 |
| Ex. 11 | Toluene | 2.851 |
| Ex. 12 | DMAc | 3.233 |
| Ex. 13 | DMSO | 3.312 |
| Ex. 14 | γ-butyrolactone | 4.042 |
| Ex. 15 | NMP | 4.140 |
| Ex. 16 | Nil | 0.904 |

Example of Fluorinated Compound Having Fluorination Degree of Less than 0.8 and Having Polar Group

Ex. 16

A composition obtained by mixing 186 g of HFO-1234yf and 28 g of R40 was put in a 500 mL autoclave equipped with a pressure meter and gradually heated by an external heater so that the pressure would be $1.011 \times 10^6$ Pa. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 4.

Ex. 17 to 20

In the same manner as in Ex. 1 except that the solvent was changed to a solvent as identified in Table 3, a sample was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 4.

TABLE 3

|  | Solvent used | Fluorination degree | Solvent charged amount [g] | HFO-1234yf charged amount [g] | R40 charged amount [g] |
|---|---|---|---|---|---|
| Ex. 17 | AE3000 | 0.700 | 184 | 53 | 8 |
| Ex. 18 | 2,3,3,3-tetrafluoropropanol | 0.500 | 185 | 81 | 12 |
| Ex. 19 | Novec7100 | 0.750 | 190 | 43 | 6 |
| Ex. 20 | Novec7200 | 0.643 | 179 | 39 | 6 |
| Ex. 16 | Nil | — | 0 | 186 | 28 |

TABLE 4

|  | Solvent used | Fluorination degree | Relative volatility |
|---|---|---|---|
| Ex. 17 | AE3000 | 0.700 | 1.405 |
| Ex. 18 | 2,3,3,3-tetrafluoropropanol | 0.500 | 1.837 |
| Ex. 19 | Novec7100 | 0.750 | 1.119 |
| Ex. 20 | Novec7200 | 0.643 | 1.082 |
| Ex. 16 | Nil | — | 0.904 |

As shown in Table 4, when a fluorinated solvent having a fluorination degree of less than 0.8 was used, the relative volatility was higher than in Ex. 16 in which no solvent was used. This is considered to result from transfer of R40 in the gas phase to the liquid phase by the effect of the fluorinated solvent having a fluorination degree of less than 0.8, thus leading to concentration of HFO-1234yf in the gas phase.

Example of Fluorinated Compound Having Fluorination Degree of Less than 0.9 and Having No Polar Group Ex. 21

A composition obtained by mixing 55 g of HFO-1234yf, 8 g of R40 and 195 g of $CClF_2CF_2CHClF$ (AK225cb) was put in a 500 mL autoclave equipped with a pressure meter and gradually heated by an external heater so that the pressure would be $1.011 \times 10^6$ Pa. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 6.

Ex. 22 and 23

In the same manner as in Ex. 21 except that the solvent used, and the amounts of charge of HFO-1234yf, R40 and the solvent were changed as identified in Table 5, a sample was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 6.

TABLE 5

|  | Solvent used | Fluorination degree | Solvent charged amount [g] | HFO-1234yf charged amount [g] | R40 charged amount [g] |
|---|---|---|---|---|---|
| Ex. 21 | AK225cb | 0.833 | 195 | 55 | 8 |
| Ex. 22 | AC6000 | 0.722 | 195 | 32 | 5 |
| Ex. 23 | HFC4310 | 0.833 | 198 | 45 | 7 |
| Ex. 16 | Nil | — | 0 | 186 | 28 |

TABLE 6

|  | Solvent used | Fluorination degree | Relative volatility |
|---|---|---|---|
| Ex. 21 | AK225cb | 0.833 | 1.441 |
| Ex. 22 | AC6000 | 0.722 | 1.120 |
| Ex. 23 | HFC4310 | 0.833 | 1.092 |
| Ex. 16 | Nil | — | 0.904 |

As shown in Table 6, when a fluorinated solvent having a fluorination degree of less than 0.9 was used, the relative volatility was higher than in Ex. 16 in which no solvent was used. This is considered to result from transfer of R40 in the gas phase to the liquid phase by the effect of the fluorinated solvent having a fluorination degree of less than 0.9, thus leading to concentration of HFO-1234yf in the gas phase.

Example of Fluorinated Compound Having Fluorination Degree of at Least 0.8 and Having Polar Group Ex. 24

A composition obtained by mixing 34 g of HFO-1234yf, 5 g of R40 and 208 g of 1,1,1,2,2,3,4,5,5,5-decafluoro-3-methoxy-4-trifluoromethylpentane was put in a 500 mL autoclave equipped with a pressure meter and gradually heated by an external heater so that the pressure would be $1.011 \times 10^6$ Pa. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 8.

Ex. 25 to 27

In the same manner as in Ex. 24 except that the solvent was changed to a solvent as identified in Table 7, a sample was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 8.

TABLE 7

| | Solvent used | Fluorination degree | Solvent charged amount [g] | HFO-1234yf charged amount [g] | R40 charged amount [g] |
|---|---|---|---|---|---|
| Ex. 24 | Novec7300 | 0.813 | 208 | 34 | 5 |
| Ex. 25 | FC-77 | 1 | 223 | 20 | 9 |
| Ex. 26 | SV-55 | 1 | 206 | 35 | 5 |
| Ex. 27 | HT-110 | 1 | 214 | 14 | 6 |
| Ex. 16 | Nil | — | 0 | 186 | 28 |
| Ex. 30 | Nil | — | 0 | 143 | 63 |

TABLE 8

| | Solvent used | Fluorination degree | Relative volatility |
|---|---|---|---|
| Ex. 24 | Novec7300 | 0.813 | 0.774 |
| Ex. 26 | SV-55 | 1 | 0.749 |
| Ex. 16 | Nil | — | 0.904 |

TABLE 9

| | Solvent used | Fluorination degree | Relative volatility |
|---|---|---|---|
| Ex. 25 | FC-77 | 1 | 0.671 |
| Ex. 27 | HT-110 | 1 | 0.665 |
| Ex. 30 | Nil | — | 1.186 |

As shown in Tables 8 and 9, when a fluorinated solvent having a fluorination degree of at least 0.8 was used, the relative volatility was lower than 1. This is considered to result from concentration of HFO-1234yf in the liquid phase by the effect of the fluorinated solvent having a fluorination degree of at least 0.52.

Example of Fluorinated Compound Having Fluorination Degree of at Least 0.9 and Having No Polar Group Ex. 28

A composition obtained by mixing 37 g of HFO-1234yf, 5 g of R40 and 209 g of tridecafluorohexane (AC2000) was put in a 500 mL autoclave equipped with a pressure meter and gradually heated by an external heater so that the pressure would be $1.011 \times 10^6$ Pa. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Table 10.

Ex. 29

In the same manner as in Ex. 28 except that the solvent was changed to perfluorohexane, a sample was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility.

Ex. 30

A composition obtained by mixing 143 g of HFO-1234yf and 63 g of R40 was put in a 500 mL autoclave equipped with a pressure meter and gradually heated by an external heater so that the pressure would be $1.011 \times 10^6$ Pa. After the pressure in the autoclave reached the prescribed $1.011 \times 10^6$ Pa, it was maintained for a certain time to stabilize the composition in the autoclave. A sample of the composition was taken from the gas phase and the liquid phase, and HFO-1234yf and R40 were analyzed by gas chromatography to measure the compositional ratios of the two. From the compositional ratios of the two, the relative volatility was obtained by the formula to obtain a relative volatility. The results are shown in Tables 9, 10 and 12.

TABLE 10

| | Solvent used | Fluorination degree | Solvent charged amount [g] | HFO-1234yf charged amount [g] | R40 charged amount [g] |
|---|---|---|---|---|---|
| Ex. 28 | AC2000 | 0.929 | 209 | 25 | 11 |
| Ex. 29 | PF-5060 | 1 | 210 | 59 | 9 |
| Ex. 16 | Nil | — | 0 | 186 | 28 |
| Ex. 30 | Nil | — | 0 | 143 | 63 |

TABLE 11

| | Solvent used | Fluorination degree | Relative volatility |
|---|---|---|---|
| Ex. 29 | PF-5060 | 1 | 0.788 |
| Ex. 16 | Nil | — | 0.904 |

TABLE 12

| | Solvent used | Fluorination degree | Relative volatility |
|---|---|---|---|
| Ex. 28 | AC2000 | 0.929 | 0.987 |
| Ex. 30 | Nil | — | 1.186 |

As shown in Table 11, when a fluorinated solvent having a fluorination degree of at least 0.9 was used, the relative volatility was lower than in Ex. 16 in which no solvent was used. Further, as shown in Table 12, when a fluorinated solvent having a fluorination degree of at least 0.9 was used, the relative volatility was lower than in Ex. 30 in which no solvent was used. This is considered to result from concentration of HFO-1234yf in the liquid phase by the effect of the fluorinated solvent having a fluorination degree of at least 0.9.

<Extractive Distillation>

A composition 1 containing HFO-1234yf and R40 is supplied to an extractive distillation tower 2 operated under elevated pressure. Of the extractive distillation tower 2, the number of theoretical plates and the operation conditions are properly set depending upon the solvent to be used, the purity of HFO-1234yf desired as a distillate 4, etc. The composition 1 supplied to the extractive distillation tower 2 is distilled while being contacted with an extracting agent 3 as an extraction solvent. In a case where an extraction solvent having high compatibility with R40 is used as an extracting agent 3, a distillate 4 having an increased concentration of HFO-1234yf than the composition 1 can be obtained from the top of the distillation tower, and a bottom product 5 having an increased concentration of R40 than the composition 1 can be obtained.

Further, in a case where an extraction solvent having high compatibility with HFO-1234yf is used as an extracting agent 3, a distillate 4 having a higher purity of R40 than the composition 1 can be obtained from the top of the distillation tower, and a bottom product 5 having an increased concentration of HFO-1234yf than the composition 1 can be obtained. By supplying the bottom product to a solvent recovery tower 6 operated under elevated pressure, when an extraction solvent having high compatibility with R40 is used as an extracting agent 3 in the extractive distillation tower 2 for example, a distillate 7 having an increased concentration of R40 than the composition 1 can be obtained from the top of the distillation tower. Further, by supplying the bottom product 5 to the solvent recovery tower 6 operated under elevated pressure, when an extraction solvent having high compatibility with HFO-1234yf is used as an extracting agent 3 in the extractive distillation tower 2 for example, a distillate 7 having a higher purity of HFO-1234yf than the composition 1 can be obtained from the top of the distillation tower.

Further, from the tower bottom of the solvent recovery tower 6, an extraction solvent containing substantially no HFO-1234yf and R40 is recovered as a bottom product 8, and the obtained bottom product is heated or cooled by a heat exchanger 9 as the case requires and is supplied to the extractive distillation tower 2 and recycled as the extracting agent 3 as the extraction solvent.

Example 1

The present invention is carried out using N-methylpyrrolidone as an extraction solvent by simulation.

To an extractive distillation tower with one theoretical plate at a solvent recovery portion, 19 theoretical plates at a concentration portion and 10 theoretical plates at a recovery portion, a composition of HFO-1234yf and R40 (in a molar ratio of 6:4) is continuously supplied at a rate of 89 g per hour from the lower portion of the concentration portion, and N-methylpyrrolidone as an extraction solvent is continuously supplied at a rate of 297 g per hour from the lower portion of the solvent recovery portion. Further, while the reflux ratio is controlled to be 15 on the tower top side, a first fraction is continuously withdrawn at a rate of 68 g per hour, and a second fraction is continuously withdrawn at a rate of 317 g per hour on the tower bottom side to conduct extractive distillation. During the extraction distillation, the pressure in the extractive distillation tower (in the system) is 0.5 MPaG (gauge pressure), the tower top temperature is 11° C., and the tower bottom temperature is 123° C.

The content of HFO-1234yf in the first fraction (a distillate 4 in FIG. 1) obtainable from the extractive distillation tower is 99.5 mol %. Further, the first fraction contains 40 mol ppm of the extraction solvent.

Whereas, the content of HFO-1234yf in the second fraction (a bottom product 5 in FIG. 1) obtainable from the extractive distillation tower is 579 mol ppm, and the content of R40 is 11.7 mol %, and the rest is substantially N-methylpyrrolidone.

The obtainable second fraction is continuously supplied at a rate of 317 g per hour to a solvent recovery tower having 15 theoretical plates, from the first plate from the bottom. Further, while the reflux ratio is controlled to be 52 on the tower top side, a third fraction is continuously withdrawn at a rate of 20 g per hour and a fourth fraction is continuously withdrawn at a rate of 297 g per hour on the tower bottom side, to conduct recovery distillation. During recovery distillation, the pressure in the solvent recovery tower (in the system) is 0.5 MPaG (gauge pressure), the tower top temperature is 20° C. and the tower bottom temperature is 277° C.

The content of R40 in the third fraction (a distillate 7 in FIG. 1) obtainable from the solvent recovery tower is at least 99.5 mol %. Whereas, the content of N-methylpyrrolidone in the fourth fraction (a bottom product 8 in FIG. 1) obtainable from the solvent recovery tower is at least 99.7 mol %. The obtainable fourth fraction is recycled to the extraction distillation tower.

Example 2

The present invention is carried out using perchloroethylene as an extraction solvent by simulation.

To an extractive distillation tower with one theoretical plate at a solvent recovery portion, 24 theoretical plates at a concentration portion and 5 theoretical plates at a recovery portion, a composition of HFO-1234yf and R40 (in a molar ratio of 6:4) is continuously supplied at a rate of 89 g per hour from the lower portion of the concentration portion, and perchloroethylene as an extraction solvent is continuously supplied at a rate of 829 g per hour from the lower portion of the solvent recovery portion. Further, while the reflux ratio is controlled to be 10 on the tower top side, a first fraction is continuously withdrawn at a rate of 61 g per hour, and a second fraction is continuously withdrawn at a rate of 857 g per hour on the tower bottom side to conduct extractive distillation. During the extraction distillation, the pressure in the extractive distillation tower (in the system) is 0.5 MPaG (gauge pressure), the tower top temperature is 14° C., and the tower bottom temperature is 141° C.

The content of HFO-1234yf in the first fraction obtainable from the extractive distillation tower is 99 mol %. Further, the first fraction contains 0.5 mol % of the extraction solvent.

Whereas, the content of HFO-1234yf in the second fraction obtainable from the extractive distillation tower is 1.3 mol, and the content of R40 is 7.3 mol %, and the rest is substantially perchloroethylene.

The obtainable second fraction is continuously supplied at a rate of 857 g per hour to a solvent recovery tower having 30 theoretical plates, from the first plate from the bottom. Further, while the reflux ratio is controlled to be 2 on the tower top side, a third fraction is continuously withdrawn at a rate of 40 g per hour and a fourth fraction is continuously withdrawn at a rate of 817 g per hour on the tower bottom side, to conduct recovery distillation. During recovery distillation, the pressure in the solvent recovery tower (in the system) is 0.2 MPaG (gauge pressure), the tower top temperature is 44° C. and the tower bottom temperature is 147° C.

The content of R40 in the third fraction obtainable from the solvent recovery tower is at least 68 mol %. Whereas, the content of perchloroethylene in the fourth fraction obtainable from the solvent recovery tower is at least 98 mol %. The obtainable fourth fraction is recycled to the extraction distillation tower.

Example 3

The present invention is carried out using 1,3-dichloro-1,1,2,2,3-pentafluoropropane (AK225cb) as an extraction solvent by simulation.

To an extractive distillation tower with 5 theoretical plates at a solvent recovery portion, 40 theoretical plates at a concentration portion and 5 theoretical plates at a recovery portion, a composition of HFO-1234yf and R40 (in a molar ratio of 6:4) is continuously supplied at a rate of 89 g per hour from the lower portion of the concentration portion, and 1,3- dichloro-1,1,2,2,3-pentafluoropropane as an extraction solvent is continuously supplied at a rate of 2,029 g per hour from the lower portion of the solvent recovery portion. Further, while the reflux ratio is controlled to be 1.5 on the tower top side, a first fraction is continuously withdrawn at a rate of 63 g per hour, and a second fraction is continuously withdrawn at a rate of 2,055 g per hour on the tower bottom side to conduct extractive distillation. During the extraction distillation, the pressure in the extractive distillation tower (in the system) is 0.5 MPaG (gauge pressure), the tower top temperature is 15° C., and tower bottom temperature is 96° C.

In the first fraction obtainable from the extractive distillation tower, R40 is not contained, and the content of HFO-1234yf is 99.8 mol %. Further, the first fraction contains 0.2 mol % of the extraction solvent.

Whereas, the content of HFO-1234yf in the second fraction obtainable from the extractive distillation tower is 0.5 mol %, and the content of R40 is 3.9 mol %, and the rest is substantially AK-225cb.

The obtainable second fraction is continuously supplied at a rate of 2,055 g per hour to a solvent recovery tower having 40 theoretical plates, from the first plate from the bottom. Further, while the reflux ratio is controlled to be 111 on the tower top side, a third fraction is continuously withdrawn at a rate of 27 g per hour and a fourth fraction is continuously withdrawn at a rate of 2,028 g per hour on the tower bottom side, to conduct recovery distillation. During recovery distillation, the pressure in the solvent recovery tower (in the system) is 0.2 MPaG (gauge pressure), the tower top temperature is 23° C. and the tower bottom temperature is 78° C.

The content of R40 in the third fraction obtainable from the solvent recovery tower is at least 87 mol %.

Whereas, the content of AK-225-cb in the fourth fraction obtainable from the solvent recovery tower is at least 99 mol %. The obtainable fourth fraction is recycled to the extraction distillation tower.

INDUSTRIAL APPLICABILITY

According to the method for separating and purifying 2,3,3,3-tetrafluoropropene and chloromethane from a composition containing them by using an extraction solvent of the present invention, a high purity product can be obtained efficiently, and the method is industrially useful.

This application is a continuation of PCT Application No. PCT/JP2013/081448, filed on Nov. 21, 2013, which is based upon and claims the benefit of priority from Japanese Patent Application No. 2012-285248 filed on Dec. 27, 2012. The contents of those applications are incorporated herein by reference in their entireties.

REFERENCE SYMBOLS

1: composition, 2: extractive distillation tower, 3: extracting agent, 4: distillate, 5: bottom product, 6: solvent recovery tower, 7: distillate, 8: bottom product, 9: heat exchanger.

The invention claimed is:

1. A method for producing 2,3,3,3-tetrafluoropropene, the method comprising contacting an azeotropic composition or azeotrope-like composition of 2,3,3,3-tetrafluoropropene and chloromethane with an extraction solvent to obtain 2,3,3,3-tetrafluoropropene containing substantially no chloromethane.

2. The method according to claim 1, wherein as the extraction solvent, at least one compound selected from the group consisting of a hydrocarbon, a chlorinated hydrocarbon, an alcohol, an ether, a nitrile, a ketone, a carbonate, an amine, an ester and a sulfoxide, which contains no fluorine atom, is used, a fluorinated compound having a fluorination degree of less than 0.8 and having a polar group is used, or a fluorinated compound having a fluorination degree of less than 0.9 and having no polar group is used.

3. The method according to claim 2, wherein the hydrocarbon is pentane, hexane, heptane, octane, nonane, decane, undecane or dodecane, the chlorinated hydrocarbon is dichloromethane, trichloromethane, perchloromethane, 1,2-dichloropropane or perchloroethylene, the alcohol is methanol, ethanol, propanol, butanol or pentanol, the ether is 1,3-dioxolane or tetrahydrofuran, the nitrile is acetonitrile, the ketone is acetone, methyl ethyl ketone, diethyl ketone or methyl isobutyl ketone, the carbonate is dimethyl carbonate, the amine is dimethylformamide, dimethylacetamide, N-methylpyrrolidone or N-formylmorpholine, the ester is γ-butyrolactone, and the sulfoxide is dimethyl sulfoxide.

4. A method for producing chloromethane containing substantially no 2,3,3,3-tetrafluoropropene from an azeotropic composition or azeotrope-like composition of 2,3,3,3-tetrafluoropropene and chloromethane, the method comprising contacting the composition with an extraction solvent.

5. The method according to claim 4, wherein as the extraction solvent, a fluorinated compound having a fluorination degree of at least 0.8 and having a polar group is used, or a fluorinated compound having a fluorination degree of at least 0.9 and having no polar group is used.

* * * * *